(12) United States Patent
Doody

(10) Patent No.: US 6,603,997 B2
(45) Date of Patent: Aug. 5, 2003

(54) PROBE PENETRATION DETECTOR AND METHOD OF OPERATION

(76) Inventor: Michael C. Doody, 4203 Towanda Trail, Knoxville, TN (US) 37919

(*) Notice: Subject to any disclaimer, the term of this patent is extended or adjusted under 35 U.S.C. 154(b) by 0 days.

(21) Appl. No.: 10/002,364

(22) Filed: Nov. 2, 2001

(65) Prior Publication Data

US 2003/0088186 A1 May 8, 2003

(51) Int. Cl.[7] .................................................. A61B 5/05
(52) U.S. Cl. .......................................................... 600/547
(58) Field of Search ............................................ 600/547

(56) References Cited

U.S. PATENT DOCUMENTS

| | | | |
|---|---|---|---|
| 4,691,571 A | * 9/1987 | Matzuk | 73/632 |
| 4,966,578 A | 10/1990 | Baier et al. | |
| 5,139,519 A | 8/1992 | Kalb | |
| 5,399,159 A | 3/1995 | Chin et al. | |
| 5,421,821 A | 6/1995 | Janicki et al. | |
| 5,423,741 A | 6/1995 | Frank | |
| 5,549,546 A | 8/1996 | Schneider et al. | |
| 5,635,852 A | 6/1997 | Wallace | |
| 5,800,381 A | 9/1998 | Ognier | |
| 6,193,692 B1 | 2/2001 | Harris et al. | |
| 6,314,315 B1 | * 11/2001 | Hung et al. | 600/547 |
| 6,337,994 B1 | * 1/2002 | Stoianovice et al. | 600/547 |

* cited by examiner

Primary Examiner—Max F. Hindenburg
Assistant Examiner—Pamela L. Wingood
(74) Attorney, Agent, or Firm—Pitts & Brittian, P.C.

(57) ABSTRACT

A probe penetration detector system and method of operation is disclosed for verifying the location of a probe within a patient during a surgical procedure. The system includes an electrically conductive antenna such as a probe adapted for insertion into body tissue and into a body cavity. A transmitter generates transmitted signals of a selected frequency range that are transmitted to the probe by an electrical connection or inductive coupling between the probe and transmitter for optimizing the conductance of transmitted signals to the probe. As the antenna probe is inserted through the body tissue and into a body cavity, a detector monitors feedback signals of energy reflected from the probe. As the feedback signals change in relation to the antenna probe location, an operator determines when the feedback signals are optimized, therefore providing notification that the antenna probe is positioned within a preferred tissue layer or body cavity.

20 Claims, 7 Drawing Sheets

PROBE PENETRATION DETECTOR AND METHOD OF OPERATION

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF INVENTION

1. Field of Invention

This invention relates generally to the field of surgery, and more particularly to an apparatus for detection of a probe penetration into a body cavity.

2. Description of Related Art

Prior techniques for surgery requiring insertion of a needle or a small diameter probe into and through the tissue layers of a patient include laparoscopic surgery with a laparoscope inserted into the interior of the abdominal cavity. Another surgical technique includes insertion of a verres needle through tissue layers and into the abdominal cavity at about the umbilical region as a part of an insufflation technique, which is the act of blowing a vapor, gas, and/or air into a body cavity such as the abdominal cavity for sufficient distension of the cavity to allow for examination and manipulation of the cavity contents. Insertion techniques for injections of medications include insertion of needle and/or a cannula/catheter through the skin and into blood vessels or other body cavities for injection of fluids. Each of the above insertion techniques require the practitioner to be able to judge by the feel of the insertion of the needle as to whether the needle end finds the target vein, layer of tissue, or body cavity. For example, during investigations of the abdominal cavity, a practitioner must determine the progress of insertion of the penetrating needle end through the tissue layers of the umbilical region of the abdominal cavity.

The prior techniques utilized by practitioners include detection of sound as the needle end penetrates, and/or the utilization of touch and feel of the physical resistance, or lack of resistance, against the needle end during penetration. An additional prior technique includes measuring changes in pressure maintained at the penetrating end of a verres needle during penetration of the multiple layers of the umbilical region of the abdomen. The multiple layers of the umbilical region include the outer skin layer, a fat cell layer of variable thickness, a fascia layer of variable tissue thickness and abdominal muscles, a peritoneum layer, and the abdominal cavity. Each of the layers of the umbilical region may vary in depth between patients, and there may be the presence of scar tissue, therefore the penetration of a needle or a similar probe during the insufflation technique requires an extremely delicate sequence of steps.

It is beneficial to medical practitioners to have a reliably reproducible monitoring system having feedback notification that indicates to an operator when each tissue layer is penetrated and when a body cavity is penetrated by an insertion end of a needle or probe. Further, it is beneficial to have a method for operation of a system utilized for monitoring the stages of penetration of an insertion end of a needle or probe through each one of a plurality of outer layers covering a body cavity of a patient.

BRIEF SUMMARY OF INVENTION

Other subjects and advantages will be accomplished by the present invention which includes a probe penetration detector system and a method of operation of the probe penetration detector system during surgical procedures. The detector system includes an electrically conductive probe, cannula, or needle which also serves as an antenna adapted for being inserted a selected depth into the body tissue and body cavity of the patient, and a transmitter for generation of a plurality of radio frequency signals transmitted to the antenna. The system further includes an electrical connection between the antenna and the transmitter, and a detector to monitor a selected feedback parameter for the antenna, with the detector providing notification of the selected feedback parameter to the operator corresponding to the proximate location of the probe, cannula, or needle. Notification of the selected feedback parameter to the operator provides an indicator of the depth of insertion of the probe, cannula, or needle antenna into the body tissue and body cavity of the patient.

More specifically, an embodiment of the electrically conductive probe includes a probe penetration unit, such as a cannula or needle, having a probe connected to a transmitter providing a plurality of signals of a selected frequency to the probe as the probe is inserted through each one of a plurality of tissue layers covering a body cavity. The detector includes analyzer circuitry and software to aid in determining when the probe has reached a location in the body at which the signal reflected from the probe approaches a characteristic value.

For example, the analyzer circuitry can calculate a standing wave ratio of the radio frequency signals transmitted to the probe compared to the, feedback parameter signals reflected from the probe. Circuitry coupled with audio and/or visual notification equipment is provided to notify the operator of the feedback parameter signals as the probe is inserted through each one of a plurality of the tissue layers, and to notify the operator that the probe is inserted into the appropriate body cavity of a patient.

BRIEF DESCRIPTION OF SEVERAL VIEWS OF THE DRAWINGS

The above mentioned features of the invention will become more clearly understood from the following detailed description of the invention contained herein, read together with the drawings in which.

DETAILED DESCRIPTION OF THE INVENTION

Figure 1:
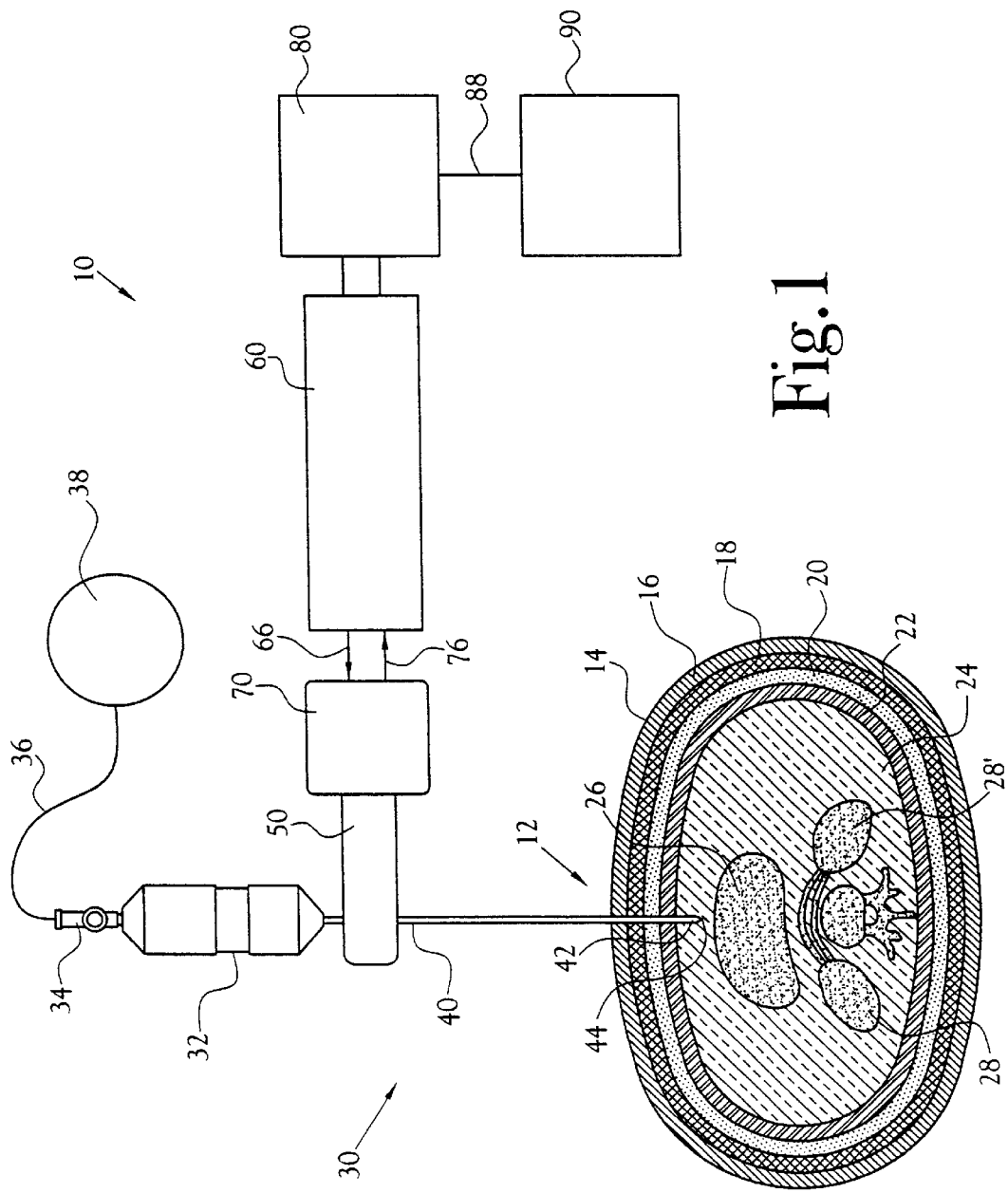
FIG. 1 is a side perspective view of one embodiment of a probe penetration detector system of the present invention.
Figure 2:
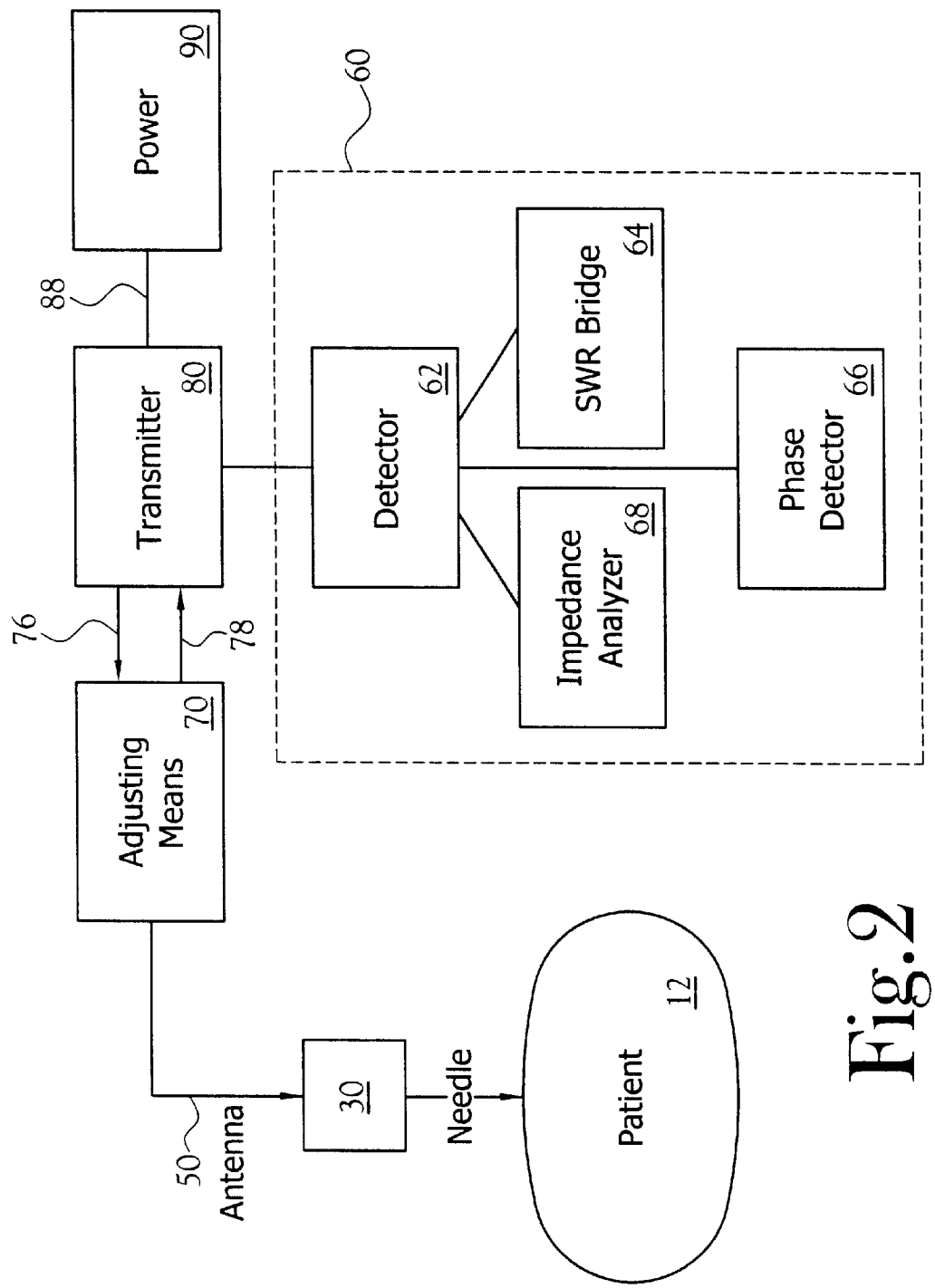
FIG. 2 is a schematic, view of the steps of a method of operation of the probe penetration detector system of FIG. 1.

A probe penetration detector system and method of operation is disclosed incorporating various features of the present invention as illustrated generally at 10 in FIG. 1. The probe penetration detector system 10 includes a skin and tissue probe unit including a probe, cannula, or needle serving as an antenna and a conductor. One example of a probe, cannula, or needle serving as an antenna includes a verres needle unit 30 that is utilized for surgical examination of a patient's body cavity 24. One embodiment provides for the insertion of a distal penetration end 42 of the verres needle unit 30 through the layers of tissue of an umbilical region 12 of the patient's abdomen. The layers of tissue covering the umbilical region 12 typically includes an outer or first surface layer of skin 14, a second layer of fat cells 16, followed by a fascia layer 18 and a layer of muscle 20. The layers of fascia and muscle may vary significantly in thickness between patients. An inner layer includes a peritoneum 22 that forms the lining of the abdominal cavity 24.

One embodiment of a probe serving as an antenna and a conductor includes the verres needle unit 30 positioned to be inserted through the respective layers of tissue of the patient, with the needle or probe length between the proximal end 40 and the distal penetration end 40 42 serving as an antenna when attached by a properly grounded electrical conductor 50. A transmitter 80 is attachable to the electrical conductor 50 for transmission of a plurality of signals of a selected frequency to the antenna. As illustrated in FIG. 1, the verres needle unit 30 includes associated equipment known to those skilled in the art, such as a housing 32, a valve 34, a fluid or gas feeder line 36, and a fluid or gas storage reservoir 38. The needle or probe serving as an antenna includes a proximal end 40 that is attachable to an electrical connector arm 50 and includes a distal penetration end 42. The penetration end 42 may includes a fluid flow passage therein, such as a dispensing hole 44 for dispensing a fluid such as liquid or gas from the fluid or gas storage reservoir 38 into the body cavity when the operator determines that the penetration end 42 is positioned properly upon review of the plurality of signals including selected feedback parameters such as impedance and standing wave ratio of the needle unit 30.

Figure 4:
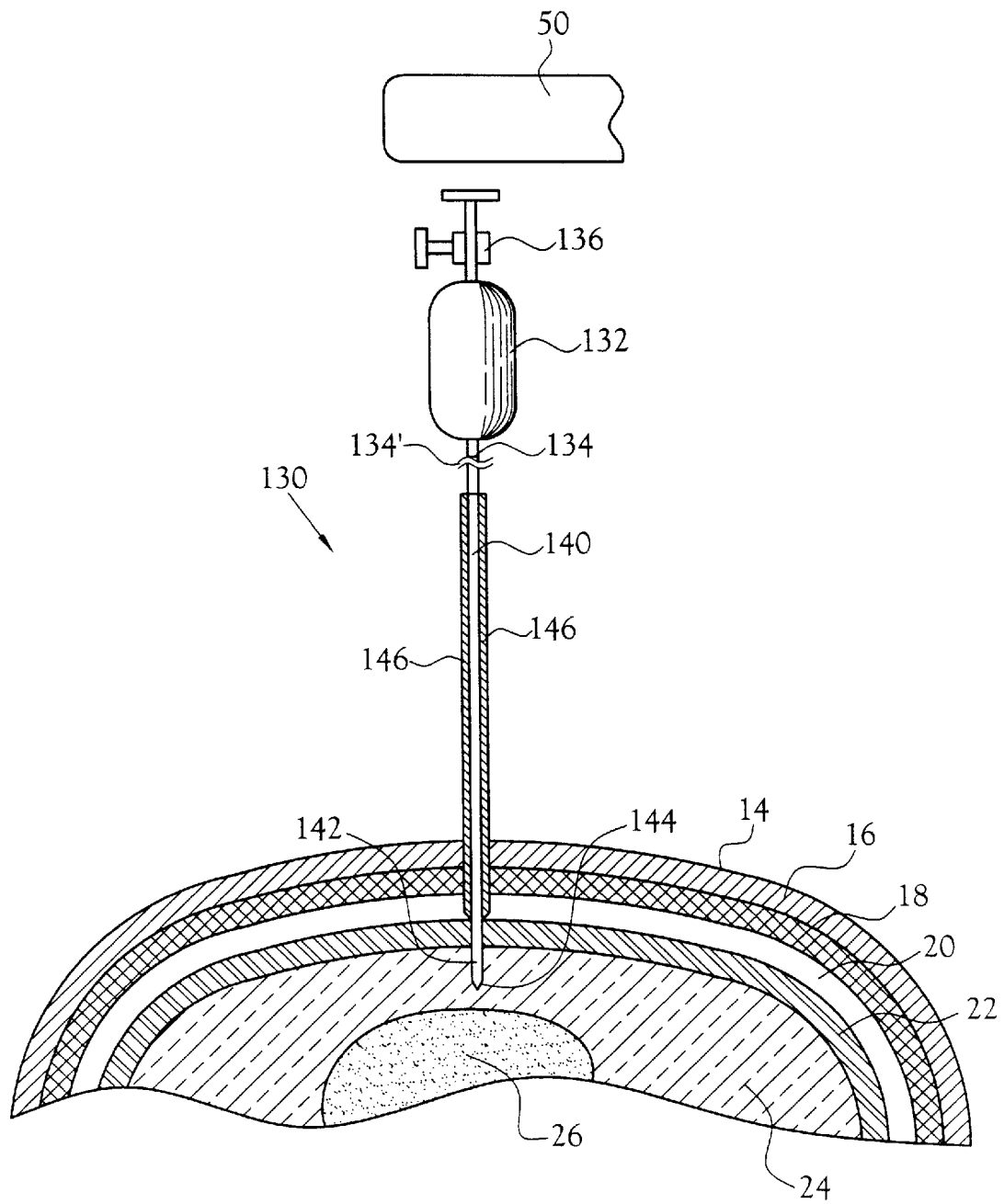
FIG. 4 is a side perspective view of an additional embodiment of a probe including a needle having insulation thereon, of the probe penetration detector system of FIG. 1.

An additional embodiment of a probe serving as an antenna and a conductor includes an insulated probe, cannula, or needle 130 having a selected base length portion 140 enclosed in an insulating layer 146 (see FIG. 4). The needle 130 includes a handle portion 132, a junction 134, and a valve 136 at a manipulation end of the needle 130. The junction 134 include a direct electrical connection of the base length portion 140 to the handle portion 132, for capacitive coupling with an electrical connector arm 50'. An alternative embodiment for the junction 134 includes a gap junction 134' to allow inductive coupling across the gap junction 134' for coupling of the base length portion 140 with an electromagnetic coil(not shown) for transmission of input signals to the base length portion 140, or for receiving of feedback parameter signals reflected from the base length portion 140. An uninsulated needle insertion end 142 provides optimal electrical coupling with each respective layer of tissue 14, 16, 18, 20, 22 through which the insertion end 142 is inserted. The uninsulated insertion end 142 provides a probe that precisely monitors the reactance values of each respective layer of tissue that is contacted. As the probe, cannula, or needle 130 having an insulated base length 140 is inserted through each layer of tissue, the reactance values detected at the insertion end. 142 are isolated from the reactance values for the layers of tissue above the insertion end 142. The insertion end 142 may include a dispensing hole 144 therein. An alternative insertion end for a verres needle may be retractable (not shown).

A transmitter 80 includes circuitry and a shielded connection 88 to a power source 90 for providing electrical power for generating a plurality of signals at a selected radio frequency. The transmitter 80 includes circuitry for transmitting the plurality of signals to the probe penetration unit serving as an antenna. The magnitude and frequency of the plurality of signals are adjustable by an operator. The range of radio frequencies of the plurality of signals may include a range of about 34 MHZ up through about 3000 MHZ and higher.

The probe penetration detector system 10 includes a detector 60 having circuitry for measuring changes in one or more selected feedback parameters from the needle or probe serving as an antenna (see FIG. 1). It will be recognized by one skilled in the art that any of the following parameters is indicative of a reliable measurement of the performance of a probe serving as an antenna, with the performance of the probe antenna dependent on the position of the probe penetration end 42, or alternatively the probe insertion end 142 within a layer of tissue or within a targeted body cavity. The selected feedback parameters may include any one or combination of the following parameters: voltage standing wave ratio (VSWR), angle of reflective coefficient, reactance, impedance, phase shift coefficient, return power loss, reflected power, reflection coefficient, resistance, capacitance, inductance, transmission loss, time domain reflectometry, and/or additional parameters related to radio frequency transmissions as known to those skilled in the art. In one embodiment, a detector 60 includes circuitry that measures the appropriately selected feedback parameter, and includes audio and/or visual display notification equipment that issues alert signals and/or displays the VSWR, reactance, and/or any of the parameters identified above, or other parameters related to radio frequency transmissions and antenna performance as known to those skilled in the art. The display notification equipment may include a visual display such as a display monitor or graphing equipment for displaying the selected feedback parameter, as illustrated in the graphs of FIGS. 3a–3g. The y-axis of FIGS. 3a–3e, entitled VSWR for voltage standing wave ratio, is a unit-less value for standing wave voltage ratio. The y-axis of FIGS. 3f–3g, entitled Return Loss, is in decibel (db). The x-axis of FIGS. 3a–3g is a wavelength value measured in megahertz.

Figure 3A:
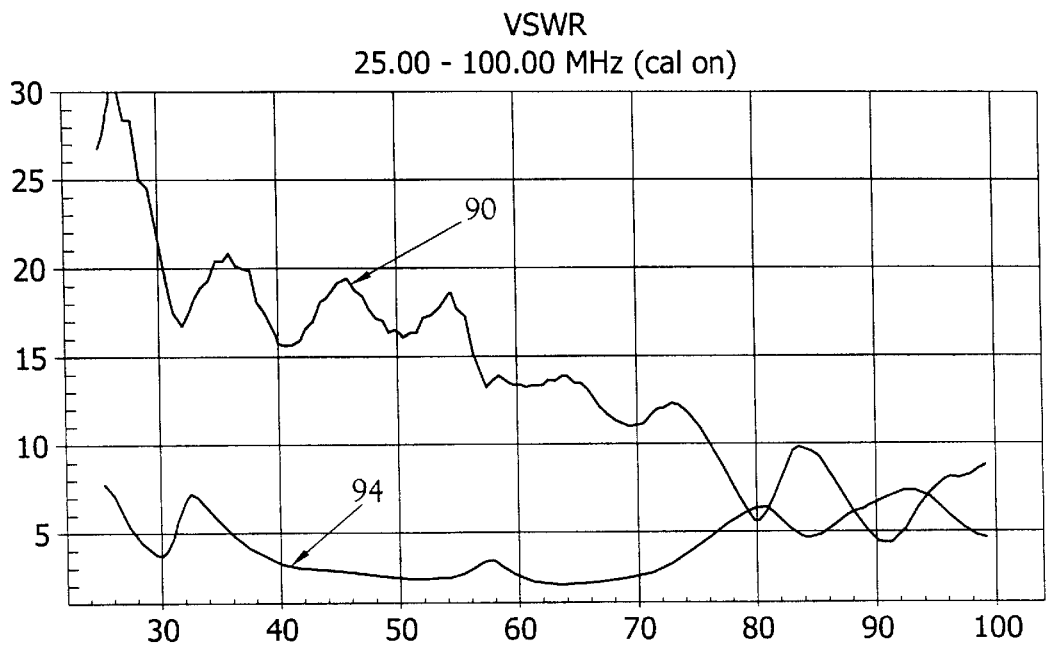
FIGS. 3a–3g are graphical representations of changes in a feedback parameter as a probe penetrates through skin, tissue layers, and into a body cavity of a patient.
Figure 3B:
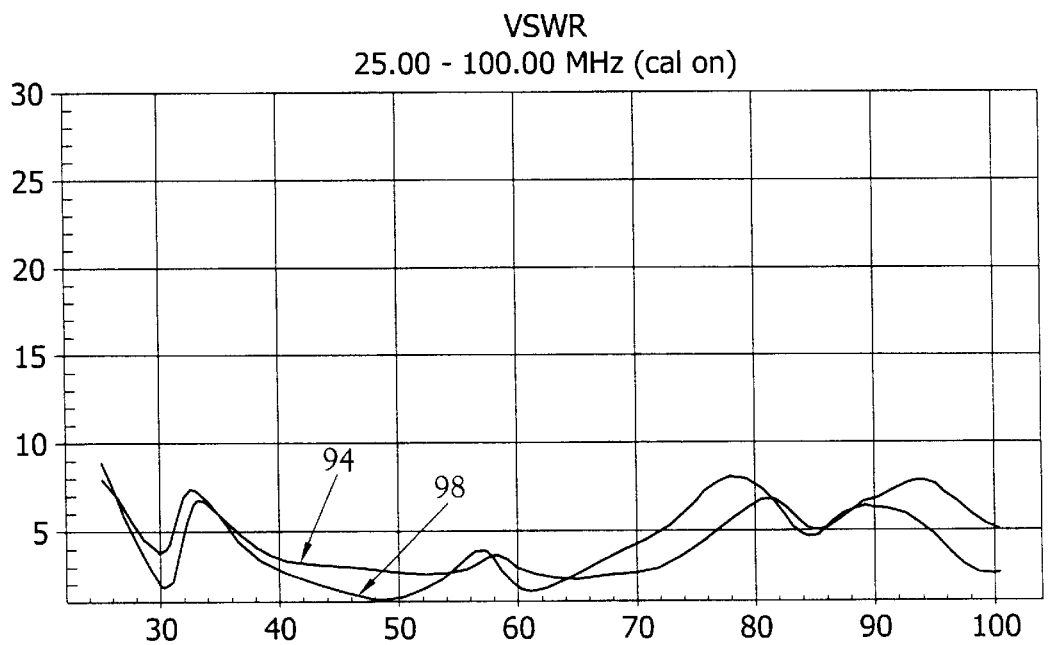
Figure 3C:
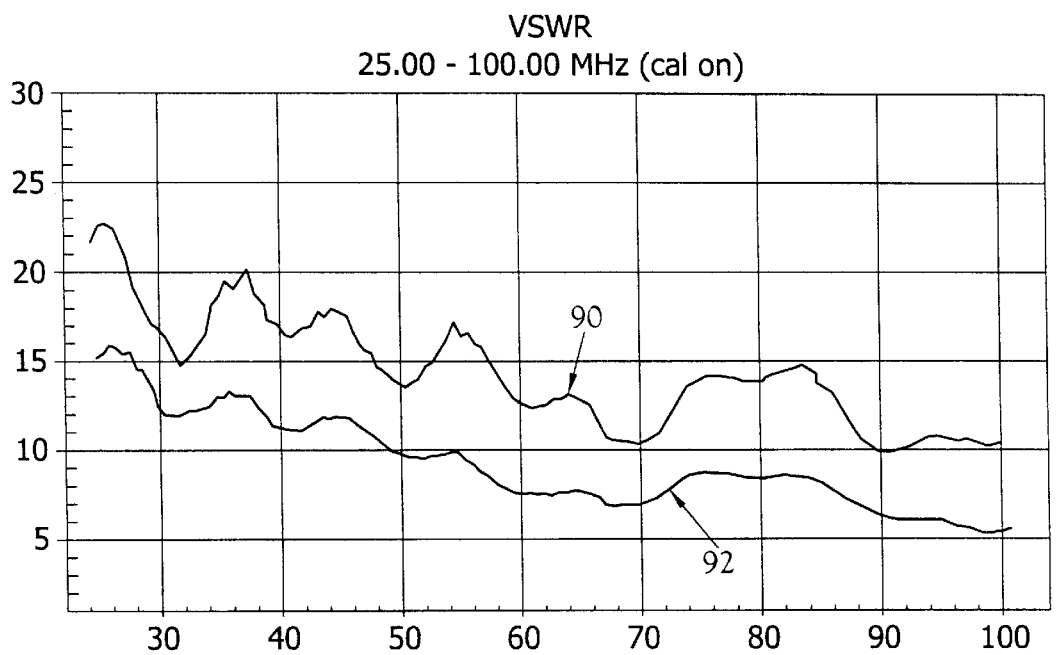
Figure 3D:
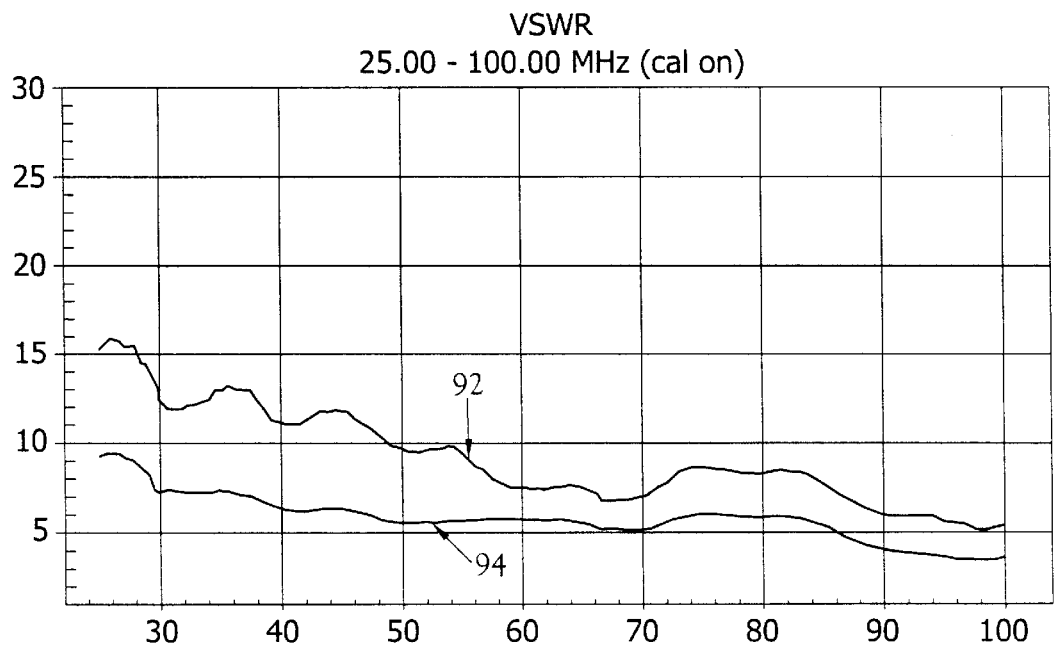
Figure 3E:
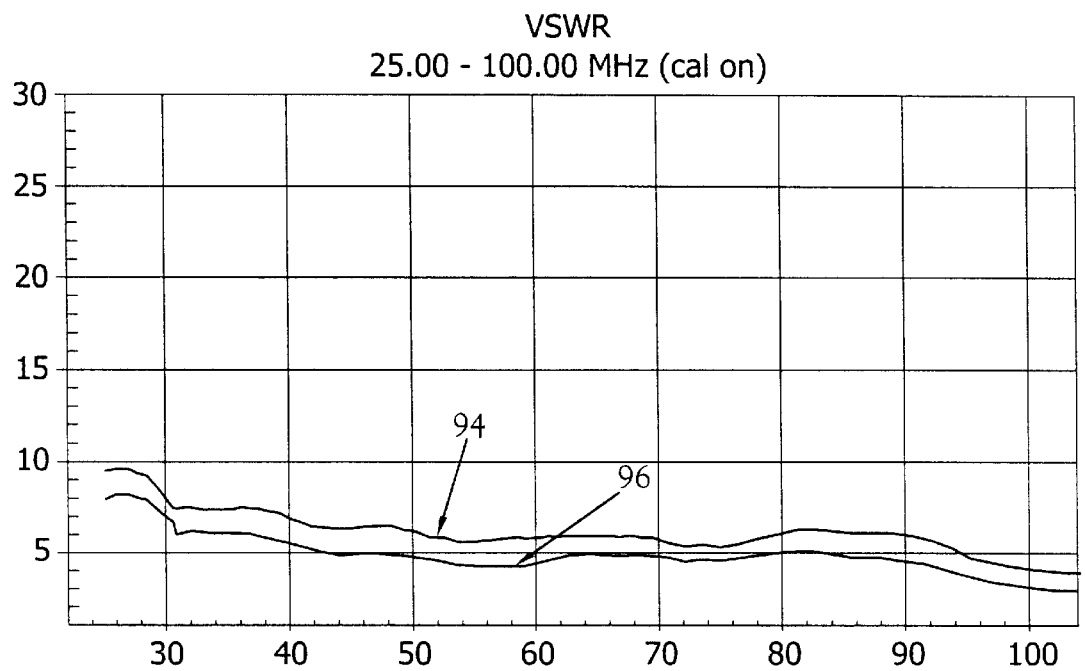
Figure 3F:
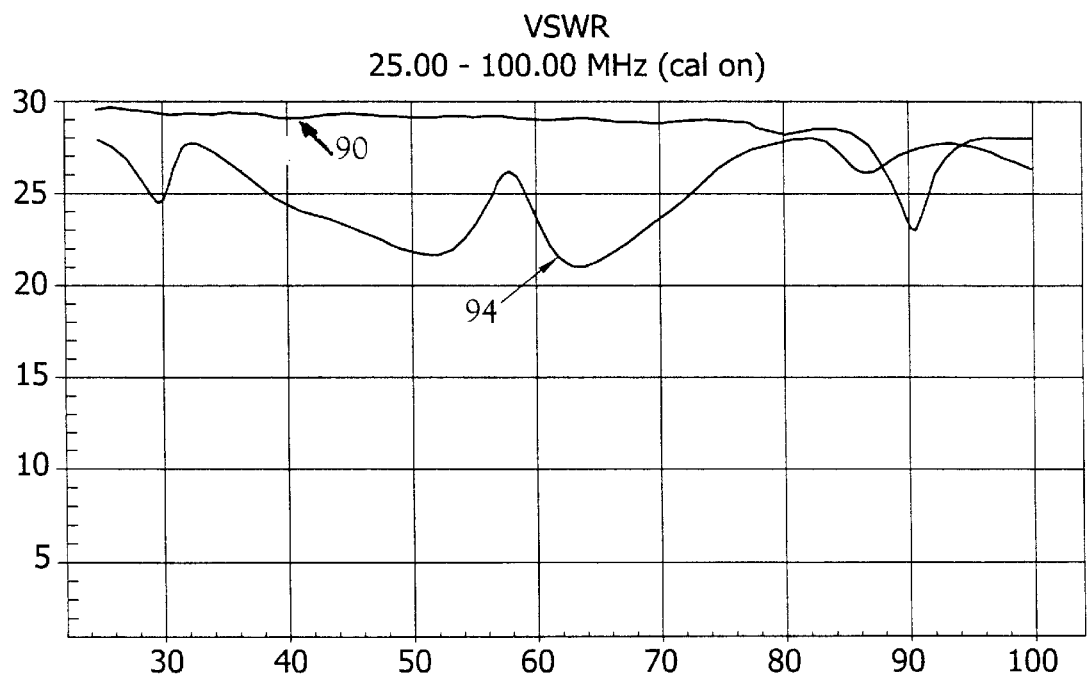
Figure 3G:
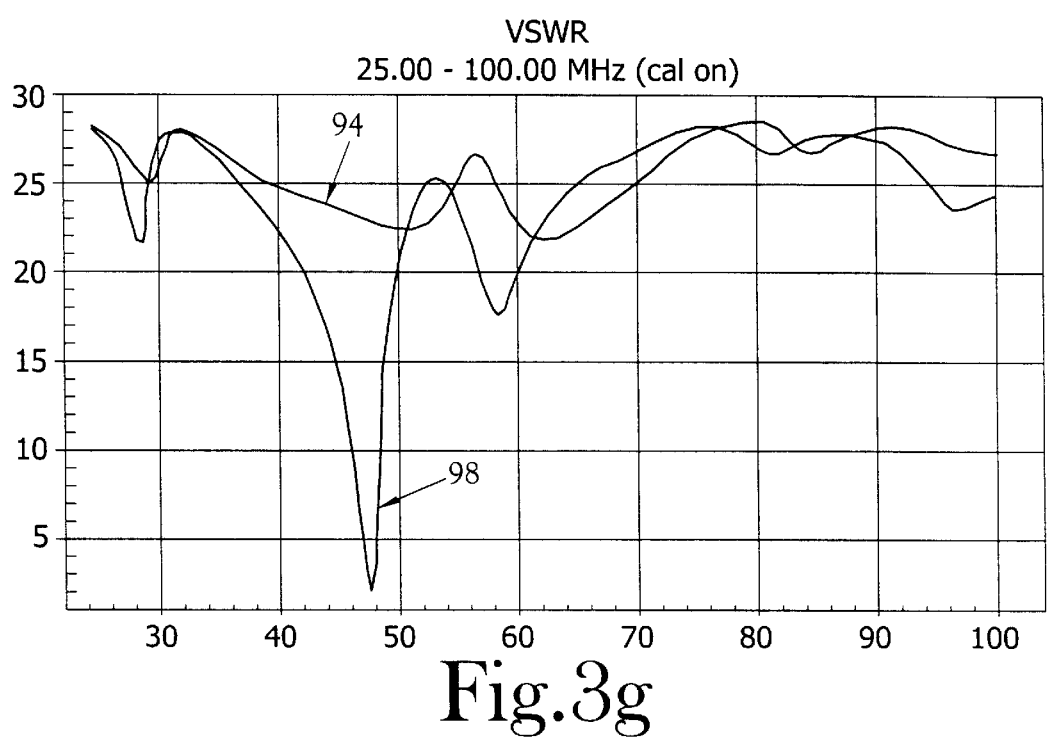

Experiments with the probe penetration detector system 10 have confirmed that probe, cannula, or needle unit 30 has a characteristic impedance value 91 when receiving a voltage signal while suspended in air (see FIGS. 33a, 3c and 3f), with a different impedance 92 obtained when the needle unit 30 is placed on a patient's skin (see FIGS. 3c and 3d), or placed below the patient's skin (see FIGS. 3a, 3b, 3d). Therefore, there is coupling of the signal transmission properties of the probe, cannula, or needle unit 30 with the signal transmission properties of a patient's body, which are measured as VSWR, angle of reflective coefficient, reactance, impedance, phase shift coefficient, return power loss, reflected power, reflection coefficient, resistance, capacitance, inductance, transmission loss, time domain reflectometry, and/or another parameter selected by the medical practitioner. Further, each of the layers of tissue provide a different impedance for the needle unit 30 having a selected frequency signal transmitted thereto. Therefore, an impedance 92 when the needle penetration end 42 is positioned on the skin (see FIGS. 3c, and 3d), compared to an impedance 94 when the needle is through the skin (see FIGS. 3a, 3b, 3d, 3e, 3f and 3g), or placed deeper into respective layers of tissue of a patient. In addition, the probe, cannula, or needle unit 30 will register a low impedance 98 during penetration into the peritoneum 22 (see FIGS. 3b and 3g), as compared to an impedance 96 during insertion into a small cavity such as a vein (see FIG. 3e), with the coupling of the needle unit 30 and the cavity providing attenuation of signals approaching an impedance matching value of a preselected value. Therefore, when the medical practitioner seeks confirmation that the needle unit 30 is positioned in the targeted body cavity, for verification to proceed with a surgical procedure such as laparoscopic surgery, the practitioner need confirm that the impedance has reached impedance matching value of a preselected value.

The detected values for the feedback parameter such as standing wave ratio and the impedance are influenced by the selected length between the proximal end 40 and the penetrating end 42, which remains the same during each surgical procedure and is selected by an operator to maximize the transmission of the feedback parameter. The detected values for the feedback parameter are further influenced by the movement of the probe serving as an antenna as the probe is sequentially positioned to contact and to insert through each respective layer of tissue, and to contact the targeted body cavity of a patient. The detector 60 includes an analyzer 62, associated circuitry and software known to those skilled in the art, for analysis and computation of a standard wave ratio (SWR) by a SWR bridge 64, of the magnitude of the signal input 76 transmitted to the needle unit 30 compared to the magnitude of the feedback parameters 78 reflected from the needle unit 30. The detector 60 further includes impedance analyzer 68 and circuitry for the measurement of the complex impedance (z) in ohms of the needle unit 30 that serves as an antenna. The measurement circuitry may include a complex impedance analyzer 68 known to those skilled in the art. A typical unit that provides measurements of the VSWR, plus measuring and monitoring the return loss is an Anritsu Wiltron 331A, or comparable models that are commercially available. Other specialized instruments are available for measuring angle of reflective coefficient, reactance, complex impedance, phase shift coefficient, return power loss, reflected power, reflection coefficient, true resistance, capacitance, inductance, transmission loss, time domain reflectometry, and/or additional parameters related to radio frequency transmissions as known to those skilled in the art.

The detector 60 includes receiver circuitry for receiving and monitoring the feedback parameters 78 returned from the needle unit 30 to analyze the modifications to the feedback parameters 78 as modified by the progress of the needle unit 30 through the plurality of layers of the patient's tissue. The detector 60 also includes a phase detector 66 for detecting phase shifting between the signal input 76 transmitted to the needle unit 30 and the feedback parameters 78 reflected from the needle unit 30. The analyzer and circuitry 62 utilizes the SWR bridge 64 for comparing the wave characteristics of the selected feedback parameters 78 transmitted from the needle unit 30, to the detector 60 having the analysis circuitry 62. The resulting change of the selected feedback parameter for the probe is calculated as the probe is inserted through each respective tissue layer and body cavity of the patient. The detector 60 and analyzer 62 may include circuitry and a feedback notification device such as a visual display or an audible display that indicates by an alert signal to an operator when each tissue layer is penetrated and when a body cavity is penetrated.

A grounded electrical connection 50 is maintained between the needle unit 30 and the transmitter 80, and the detector 60 and analyzer 62. The detector 60 and analyzer 62 further includes an analysis circuitry for comparing signal changes as the penetrating end 42 is manipulated by depth adjusting element 70. When the signals are analyzed in the range of about 40 MHZ to about 70 MHZ for the use of a verres needle insertion into the abdomen, the complex impedance for the needle unit 30 is analyzed during passage through each tissue layer, and an operator will observe that the VSWR of the needle unit 30 in air is about 15 to about 22. As the needle unit 30 is placed on the outer skin layer 14, a VSWR is observed of about 7 to about 10. As the penetrating end 42 is inserted through the skin layer 14, a VSWR is observed of about 5 to about 6. When the penetrating end 42 is inserted into the peritoneum 22, a VSWR is observed of about 1 to about 4, which allows the operator to confirm that the penetrating end 42 has reached the targeted body cavity.

In the confines of an operating room, an assistant may be requested to follow the following steps to provide a probe penetration detector system 10 and to confirm that a needle penetrating end 42 is properly inserted into a selected body cavity such as an abdominal cavity 24. Power is provided by a shielded power line 88 from a power source 90. A signal frequency is selected for the transmitter 80, between about 30 MHZ up through about 3000 MHZ. One preferred range is from about 40 MHZ to about 60 MHZ. The signal input 76 is transmitted by a path including the depth adjusting element 70, the grounded electrical connection 50, to the needle unit 30 serving as an antenna. As the depth of insertion of the penetrating end 42 is adjusted by the assistant with the depth adjusting element 70, the feedback parameters 78 are transmitted from the needle unit 30 to the analyzer circuitry 62 for computation of impedance by the impedance analyzer 68 and the SWR by the SWR bridge 64. When the VSWR of the needle unit 30 approaches about 1 to about 4, the assistant may confirm that the penetrating end 42 of the needle or probe is properly inserted through the body tissue and into the body cavity selected for investigation, such as the abdominal cavity 24.

The assistant may further optimize the plurality of signals transmitted to the needle unit 30 inserted into the abdominal cavity 24 by selecting a preferred frequency range by utilizing the depth adjusting element 70 to attain a preferred-resonant frequency of about 47 MHZ from the selected range of about 40 MHZ to about 60 MHZ, to confirm by feedback signals from the needle or probe that the penetrating end 42 is inserted into a targeted body cavity, and to confirm that the penetrating end 42 remains inserted in a body cavity such as the abdominal cavity 24.

The probe penetration detector system 10 may be utilized to confirm proper insertion of the penetrating end 42 into the abdominal cavity 24 as illustrated above, and/or for insertion of spinal or epidermal catheters into the layers below or above the spinal membrane. Further, the probe penetration detector system 10 may be utilized to confirm proper insertion of a subclavian catheter in to the subclavian vein, and/or for placement of a needle, probe, cannula, or catheter into the pleural cavity of the chest, bladder, joint spaces, extremity veins or arteries, or any body cavity or tissue space of the patient.

While a preferred embodiment is shown and described, it will be understood that it is not intended to limit the disclosure to the described embodiment, but rather it is intended to cover all modifications and alternate configurations falling within the spirit and the scope of the invention as defined in the appended claims.

What is claimed is:

1. A probe penetration detector system for the surgical examination by an operator of respective layers of body tissue and a body cavity of a patient, comprising:
   an electrically conductive probe adapted for being inserted into the respective layers of body tissue and into the body cavity of the patient, said probe serving as an antenna while proximal of respective layers of body tissue and the body cavity of the patient;

a transmitter for generation of a plurality of radio frequency signals transmitted to said probe;

a connector in electrical connection with said transmitter, said connector disposed proximal of said probe for transmission by capacitive coupling of said radio frequency signals to said probe; and a detector to monitor a selected feedback parameter for said probe, said detector including circuitry for notification of said selected feedback parameter in to the operator as each respective layer of the body tissue and the body cavity is penetrated by said probe;

whereby said selected feedback parameter provides the operator with an indicator of penetration of said probe through the respective layers of body tissue and into the body cavity of the patient.

2. The probe penetration detector system of claim 1, wherein said electrically conductive probe includes a needle having a length portion and a penetration end, said length portion having insulation thereon, said penetration end being uninsulated for contact upon insertion into the body tissue and body cavity of the patient, whereby said uninsulated penetration end maintains optimal electrical coupling with each respective layers of body tissue and the body cavity through which said penetration end is inserted; and said penetration end includes a fluid flow passage therein for dispending of a fluid into the body cavity when the operator is notified by said detector of said selected feedback parameter indicating that said penetration end is inserted into the body cavity of the patient.

3. The probe penetration detector system of claim 1, wherein said transmitter includes circuitry for generation of a plurality of signals for transmission to said electrically conductive probe during penetration of said probe through the respective layers of body tissue and in the body cavity of the patient, said plurality of signals having an amplitude frequency and phase being adjustable by the operator.

4. The probe penetration detector system of claim 1, wherein said selected feedback parameter includes a parameter selected from the group consisting essentially of a voltage standing wave ratio, an impedance, a phase shift, a reactance, an inductance, a capacitance, a resistance, a transmission loss, a reflected power, a reflection coefficient, of and a return power loss for said probe.

5. The probe penetration detector system of claim 1, wherein said circuitry for notification includes a visual display of said selected feedback parameter.

6. The probe penetration detector system of claim 5, wherein said circuitry for notification further includes an audible display of said selected feedback parameter.

7. A probe penetration detector system for the surgical examination by an operator of a patient's body tissue and a body cavity of the patient, comprising:

an electrically conductive antenna including a probe penetration unit having a probe end adapted for being inserted a selected depth into the body tissue and the body cavity of the patient;

a transmitter for generation of a plurality of radio frequency signals transmitted to said antenna;

an electrical connection between said antenna and said transmitter; and a detector to monitor a standing wave ratio parameter for said antenna, said detector including circuitry for notification of said standing wave ratio parameter to the operator as each respective layer of the body tissue and the body cavity is penetrated by said probe end;

whereby said standing wave ratio parameter provides the operator with an indicator of penetration of said antenna probe end through each respective layer of the body tissue and into the body cavity of the patient.

8. A probe penetration detector system for the surgical examination by an operator of a patient's body tissue and body cavity, comprising:

an electrically conductive antenna including a probe penetration unit having a probe end adapted for being inserted a selected depth into the body tissue and body cavity of the patient;

a transmitter for generation of a plurality of signals transmitted to said antenna said transmitter includes an inductive coupling between said probe penetration unit and said transmitter;

an adjusting element disposed to position said probe penetration unit to optimize said inductive coupling between said antenna and said transmitter as said probe end is inserted through each respective layer of the body tissue and into the body cavity; and a detector to monitor an impedance parameter for said antenna, said detector including circuitry for notification of said impedance parameter to the operator;

whereby said impedance parameter provides the operator with an indicator of insertion of said antenna probe end through each respective layer of the body tissue and into the body cavity of the patient.

9. A probe penetration detector system for the surgical examination by an operator of a patient's body tissue and a body cavity, comprising:

an electrically conductive antenna including a probe penetration unit having a probe end adapted for being inserted a selected depth into the body tissue and the body cavity of the patient;

a transmitter for generation of a plurality of signals transmitted to said antenna;

an electrical connection between said antenna and said transmitter; and a detector to monitor a signal return power loss parameter for said antenna, said detector including circuitry for notification of said signal return power loss parameter to the operator;

whereby said signal return power loss parameter provides the operator with an indicator of penetration of said antenna probe end through each respective layer of the body tissue and into the body cavity of the patient.

10. A probe penetration detector system for the surgical examination by an operator of a body cavity of a patient, comprising:

a probe penetration unit having a probe end positioned to be removably inserted through each one of a plurality of tissue layers covering the body cavity of the patient;

a transmitter for transmission of a plurality of radio frequency signals to said probe penetration unit as said probe end is inserted through each one of the plurality of tissue layers, said transmitter includes an inductive coupling between said probe penetration unit and said transmitter;

a detector for receiving a plurality of output signals rebounded from said probe penetration unit, said detector provides analysis of said output signals in a comparison of said plurality of signals with said output signals to generate a standing wave ratio for said probe penetration unit as said probe end is inserted through each one of the plurality of tissue layers; and an adjusting element to position said probe penetration unit to optimize said standing wave ratio as said probe end is inserted through each one of the plurality of tissue layers;

wherein when said standing wave ratio is optimized, the insertion of said probe end into the body cavity of the patient is confirmed for the operator.

11. The probe penetration detector system of claim 10, said detector including an impedance analyzer for measuring impedance of said probe penetration unit as said probe end is inserted through each one of the plurality of tissue layers.

12. The probe penetration detector system of claim 11, wherein said transmitter including circuitry for detecting a resonant frequency for said plurality of signals transmitted to said probe penetration unit as said probe end is inserted through each one of the plurality of tissue layers.

13. The probe penetration detector system of claims 12, wherein said transmitter being adjustable by the operator to optimize said plurality of signals transmitted to said probe penetration unit, whereby the operator optimizes said standing wave ratio as said probe end is inserted through each one of the plurality of tissue layers.

14. The probe penetration detector system of claim 13, wherein said inductive coupling provides a path across a junction between said probe penetration unit and said transmitter for transmission of said plurality of signals being transmitted to said probe penetration unit, said inductive coupling provides a return pathway for said plurality of output signals rebounded from said probe penetration unit.

15. A probe penetration detector system for the surgical examination by an operator of a body cavity of a patient, comprising:
a probe penetration unit having a probe positioned to be removably inserted through each one of a plurality of tissue layers covering the body cavity of the, patient;
a transmitter for transmission of a plurality of input signals to said probe as said probe is inserted through each of the plurality of tissue layers, said transmitter is connected by an inductive coupling connection with said probe penetration unit;
a detector for receiving a plurality of output signals rebounded from said probe, said detector provides analysis of said output signals in a comparison of said plurality of input signals with said output signals to generate a standing wave ratio for said probe as said probe is inserted through each of the plurality of tissue layers;
an adjusting element for positioning said probe to optimize said standing wave ratio as said probe is inserted through each one of the plurality of tissue layers; and
an impedance analyzer for analysis of impedance of said probe as said probe is inserted through each of the plurality of tissue layers;
wherein when said standing wave ratio is optimized, the, insertion of said probe into the body cavity of the patient is confirmed for the operator.

16. The probe penetration detector system of claims 15, wherein, said transmitter being adjustable by the operator to optimize said plurality of input signals transmitted to said probe, whereby the operator optimizes said standing wave ratio of said probe as said probe is inserted through each of the plurality of tissue layers.

17. The probe penetration detector system of claim 16, wherein said inductive coupling connection provides an input pathway for said plurality of input signals being transmitted to said probe, said inductive coupling connection provides a return pathway to said detector for said plurality of output signals rebounded from said probe.

18. A method to provide confirmation of the insertion of a probe through a plurality of layers of tissue and into a body cavity of a patient during a surgical procedure, comprising the steps of:
providing a probe penetration detector system including an adjusting element for the positioning of the probe through the layers of tissue of the patient;
transmitting a plurality of input signals to the probe as the probe is adjusted in positioning through each one of the layers of tissue of the patient;
detecting a plurality of output signals rebounded from the probe, said detecting step providing an analyzing step for comparing said plurality of input signals with said output signals, said analyzing step generating a standing wave ratio for said probe is adjusted in positioning through each one of the layers of tissue of the patient; and
measuring an impedance parameter of the probe as the probe is adjusted in positioning through each one of the layers of tissue, said measuring step including measuring impedance when the probe is inserted into a body cavity of the patient.

19. The method of claim 18, wherein said providing step further including a step of calibrating the probe of said probe penetration detector system, said calibrating step including selecting a probe length that is conductive to transmitting said plurality of input signals to the patient to substantially minimize the reflected power from the probe, positioned through the layers of tissue of the patient.

20. The method of claim 18, wherein said transmitting step further including the step of inducing a resonant frequency for said plurality of input signals being transmitted to said probe, said inducing step further including providing an adjusting circuitry for said plurality of input signals being transmitted as said probe is inserted through each one of said plurality of layers of tissue.

* * * * *